United States Patent [19]

Mendoza

[11] Patent Number: 4,978,809

[45] Date of Patent: Dec. 18, 1990

[54] META-HALOGENATED DIBENZYLPHENOLS

[75] Inventor: Abel Mendoza, Midland, Mich.

[73] Assignee: The Dow Chemical Company, Midland, Mich.

[21] Appl. No.: 434,150

[22] Filed: Nov. 13, 1989

[51] Int. Cl.$^5$ .............................................. C07C 39/12
[52] U.S. Cl. .................................... 568/720; 568/718
[58] Field of Search ................................ 568/720, 718

[56] References Cited

U.S. PATENT DOCUMENTS

| | | | |
|---|---|---|---|
| 2,783,279 | 2/1957 | Chiddix | 568/720 |
| 2,798,046 | 7/1957 | Beavck et al. | 568/720 |
| 3,053,803 | 9/1962 | Jaffe et al. | 568/720 |
| 3,281,478 | 10/1966 | Farnham | 568/720 |
| 3,925,488 | 12/1975 | Shin | 568/720 |
| 4,415,724 | 11/1983 | Mark et al. | 568/720 |
| 4,532,059 | 7/1985 | Rosenberger | 568/720 |
| 4,731,423 | 3/1988 | Mendoza et al. | 568/720 |
| 4,778,936 | 10/1988 | Mizuno et al. | 568/720 |

*Primary Examiner*—Werren B. Lone

[57] ABSTRACT

Thermally stable methylene-bridged polyphenols such as 2,4-bis(4-hydroxy-3,5-dimethyl)-3,5-dibromo-6-methylphenol are prepared by contacting (1) a substituted phenol having at least one halogen substituted on the aromatic ring in a position meta to the phenolic hydroxyl and at least one halomethyl group substituted on the aromatic ring in a position ortho or para to the phenolic hydroxyl with (2) and o,o-dialkylphenol having hydrogen on the aromatic ring position which is para to the phenolic hydroxyl under alkylation conditions.

12 Claims, No Drawings

META-HALOGENATED DIBENZYLPHENOLS

BACKGROUND OF THE INVENTION

This invention relates to meta-halogenated phenols and to processes for their preparation.

Halogenated phenols are often used as fungicides, monomers and flame retardants. Certain halogenated phenols such as polybrominated phenols are used in the manufacture of brominated aromatic epoxy thermosets which are especially useful in the electronics industry.

Such polybrominated phenols are usually prepared by contacting a phenol such as bisphenol-A with bromine in methanol or aqueous acetic acid thereby producing the ortho-brominated phenols such as tetrabromobisphenol-A. However, the hydrolytic instability of the ortho-bromophenols has been observed to contribute to internal corrosion of the encapsulated parts of many electronic devices, thereby reducing or destroying the effectiveness of the electronic device employing the encapsulated parts, e.g., microelectric circuitry.

As reported in U.S. Pat. No. 4,731,423, the meta-bromophenols are known to be more hydrolytically stable than their ortho-bromo counterparts. It is, therefore, particularly desirable to employ such meta-bromophenols in epoxy thermosets used in electrical encapsulations which require a thermoset having good thermal properties, e.g., flame retarding capability and glass transition temperatures ($T_g$) of at least 155° C. as well as hydrolytic stability significantly greater than that observed for the ortho-bromophenols. A major reason for the need for higher thermal stability is the miniaturization in the art of microelectric circuitry, often called "microchip" technology. As the size of the microchips becomes increasingly smaller, the localized heat problems become increasingly greater, and thus the present encapsulation formulation properties may not be as suitable as desired.

Unfortunately, the thermally and hydrolytically stable meta-bromophenols are often difficult to prepare and yields of the desired products are usually only modest. See, for example, the methods described in U.S. Pat. Nos. 3,929,908: 3,956,403: and 4,058,570. Moreover, the methods for making the simple meta-bromophenols, which usually involve the bromination of the corresponding phenol, are essentially useless for the preparation of complex meta-bromophenols because the complex phenol precursors are decomposed upon bromination. Examples of such complex phenols are the dibenzylphenols as described in U.S. Pat. No. 4,222,884.

Therefore it would be highly desirable to provide a process for making complex meta-halophenols that cannot be made by typical bromination or chlorination processes.

SUMMARY OF THE INVENTION

The present invention, in one aspect, is a thermally stable methylene-bridged polyphenol having at least two phenolic hydroxyl moieties which are substituted on different aromatic rings wherein at least one phenolic hydroxyl is in a ring position ortho to a methylene bridge, and at least two halogens, each of which is substituted on an aromatic ring in a position meta to a phenolic hydroxyl. Hereinafter this polyphenol shall be referred to as an MBDB phenol.

In another aspect, the present invention is a process for preparing the MBDB phenol which process comprises contacting (1) a substituted phenol having at least one halogen substituted on the aromatic ring in a position meta to the phenolic hydroxyl and at least one halomethyl group substituted on the aromatic ring in a position ortho or para to the phenolic hydroxyl with (2) an o,o-dialkylphenol having hydrogen on the aromatic ring position which is para to the phenolic hydroxyl in the presence of an alkylation catalyst under conditions sufficient to form the MBDB phenol.

The MBDB phenols of this invention exhibit excellent thermal and hydrolytic stability and are therefore particularly suitable for the manufacture of epoxy resins used to make encapsulants for microelectronic devices. The MBDB phenols are also useful as precursors for monomers and as monomers for other thermoset polymers such as cyanate resins and as flame retardants for a variety of polymeric compositions.

DETAILED DESCRIPTION OF ILLUSTRATIVE EMBODIMENTS

The novel polyphenols (MBDB phenols) of the present invention preferably have at least one, and more preferably at least two, terminal phenolic moieties represented by the structural formula:

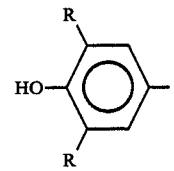

wherein each R is independently hydrogen, alkyl having from 1 to 12 carbons, cycloalkyl having from 5 to 10 carbons, aralkyl having from 8 to 12 carbons and alkoxy having 1 to 6 carbons. Further, the novel MBDB phenol preferably has a divalent connecting halogenated phenolic moiety as represented by the structural formula:

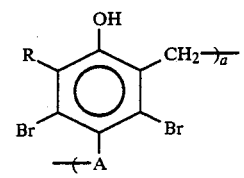

wherein A is —$CH_2$— or a covalent bond, R is as previously defined and "a" is a whole number from 1 to 10. most preferably 1. Alternatively, the halogenated phenolic moiety is monovalent and A is Br or methyl. Most preferred are the MBDB phenols represented by the structural formula:

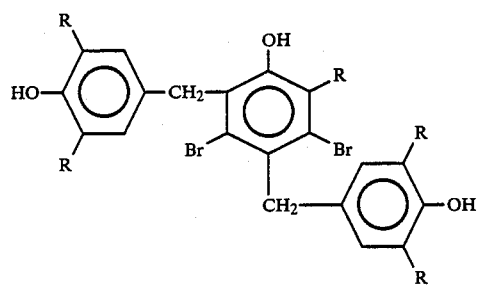

wherein R is methyl or ethyl.

The most preferred MBDB phenols are prepared by first halogenating a phenol having at least 3 alkyl substituents on an aromatic ring such as 2,4,6-trimethylphenol and then alkylating the halogenated product with a 2,6-dialkylphenol to form the desired MBDB phenol.

The halogenation step is carried out using the starting materials and conditions described in U.S. Pat. No. 4,684,752, which is incorporated by reference. Preferably, a stirred solution of the alkyl phenol in an inert organic diluent is contacted with a halogenating agent at a moderate temperature until halogenation is completed.

Examples of preferred alkyl phenols include mesitol (2,4,6-trimethylphenol), xylenol (particularly 2,6-dimethylphenol) and tetramethylbiphenol (particularly 3,5,3′,5′-tetramethylbiphenol and similar alkylphenols and methods for preparing which are described in U.S. Pat. Nos. 2,841,623; 3,360,573: 3,751,488: 3,764,630; 3,899,540 and 3,976,702. Of these alkylphenols, tetraalkylbiphenol is more preferred and mesitol is the most preferred. In addition, previously halogenated alkylphenols such as tribromomesitol and brominated tetramethylbiphenol can be further halogenated to form higher haloalkylphenols. Also, phenols such as 2-hydroxymethyl-4,6-dimethylphenol can be brominated to afford 2-bromomethyl-3,5-dibromo-4,6-dimethylphenol (ortho-tribromomesitol) using the procedure described by Fries et al., in Ann., 353, 335-356 (1907).

Halogenating agents typically employed include chlorine, bromine and other halogenating agents known to be useful for the halogenation of aromatic rings, with bromine being the most preferred halogenating agent. Inert inorganic diluents are preferably liquid hydrocarbon and halohydrocarbon such as 1,2-dichloroethane, chlorobenzene, 1,1,2-trichloroethane, dibromomethane and other similarly inert organic solvents which are liquid under the halogenation conditions.

The halogenation step is preferably carried out at a temperature in the range from about 70° C. to about 110° C. and at a pressure which permits the removal of hydrogen halide gas as it is formed during the reaction period which is from about 3 to about 5 hours. Typically the reaction pressure is atmospheric or subatmospheric. While the order of addition of ingredients is not particularly critical, it is usually preferred to slowly add the halogenating agent to the stirred alkylphenol at ambient temperature and then increase the temperature to cause reaction. In general it is not necessary to employ a halogenation catalyst, particularly if bromine is being employed.

The halogenated alkylphenols thus formed are preferably tribromomesitol (4-bromomethyl-3,5-dibromo-2,6-dimethylphenol), 3,4,5-tribromo-2-bromomethyl-6-methylphenol, 2,2′,6,6′-tetrabromo-3,3′,5′-tris(bromomethyl)-5-methylbiphenol, 2,2′,6,6′-tetrabromo-3,3′-bis(bromomethyl)-5,5′-dimethylbiphenol, 2,2′6,6′-tetrabromo-3-bromomethyl-3′,5,5′-trimethylbiphenol and other meta-halogenated alkylphenols such as described in U.S. Pat. Nos. 4,684,752 and 4,731,423.

In the alkylation step, the reaction product of the halogenation step can be employed as is or the desired halogenated product can be used in a pure form by isolating it from the other components of the reaction product and then dissolving it in an inert organic diluent. Preferably the halogenated product in essentially purified form is alkylated by contacting the reaction product with phenol or a phenol having one or more alkyl substituents in the presence of an alkylation catalyst such as a Friedel-Crafts catalyst under the conditions generally described in U.S. Pat. Nos. 4,731,423: 4,117,019: 4,251,675: 4,414,406 and 4,415,483.

Examples of preferred alkylating phenols include 2,6-dialkylphenols such as 2,6-dimethylphenol, 2-alkylphenols such as o-cresol, 4-alkylphenols such as p-cresol, and similar alkylated phenols wherein the alkyl groups have from 1 to 4 carbons, with the 2,6-dialkylphenols being more preferred and 2,6-dimethylphenol being most preferred. Examples of preferred alkylation catalysts include ferric chloride, toluenesulfonic acid and aluminum trichloride, with ferric chloride being the most preferred. Examples of preferred diluents are as previously described for the halogenation step.

The alkylation step is preferably carried out at a temperature in the range from about 20° C. to about 70° C. and at a pressure ranging from atmospheric to superatmospheric over a period from about one to about ten hours. While the order of addition of ingredients is not particularly critical, it is usually preferred to add the alkylating agent to the stirred halogenated product and then add the catalyst and heat the resulting mixture to the reaction temperature Either the halogenation step or alkylation step can be carried out in air or under an inert atmosphere such as nitrogen.

The alkylation product, i.e., the desired polyphenol, is isolated from the remaining components of the alkylation mixture using conventional techniques as illustrated in the Illustrative Embodiments. The desired polyphenol is thus usefully employed as an encapsulant in an epoxy resin formulation using the procedures and conditions described in U.S. Pat. No. 4,731,423.

Illustrative Embodiments

The following examples are given to illustrate the invention and should not be interpreted as limiting it in any way. Unless stated otherwise, all parts and percentages are given by weight.

EXAMPLE 1

A. Bromination of Mesitol

A 13.6-g (0.1 mole) portion of mesitol is dissolved in 100 ml of 1,1,2-trichloroethane which has been previously charged to a 0.5-liter flask equipped with a dropping funnel, a mechanical stirrer and a reflux condenser. To this solution is added 30.7 ml (0.6 mole) of bromine at 25° C.-31° C. with stirring over a period of a few minutes. The resultant stirred slurry is slowly heated to 90° C.-95° C. and maintained at that temperature for 4 hours. At the end of this period, 60 ml of the liquid phase of the reaction mixture containing unreacted bromine is removed by distillation under nitrogen. The residual solution is cooled and filtered to recover 20.9 g of a white solid which is determined by proton NMR and liquid chromatography to be 80 percent (area percent) of 2,4-bis(bromomethyl)-3,5-dibromo-6-methylphenol, 5 percent of 4-bromomethyl-3,5-dibromo-2,6-dimethylphenol, 6 percent of 2,6-bis(bromomethyl)-3,5-dibromo-4-methylphenol and 4 percent of 2,4,6-tris(bromomethyl)-3,5-dibromophenol. Removal of solvent from the filtrate mother liquor yields 24.2 g of solid which is similarly analyzed and determined to contain a predominant amount of the 2,4-bis(bromomethyl)-3,5-dibromo-6-methylphenol and minor amounts of the other products listed above.

B. Alkylation of 2,4-Bis(bromomethyl)-3,5-dibromo-6-methylphenol

A 4.52-g portion of the solid product from Part A containing 2,4-bis(bromomethyl)-3,5-dibromo-6-methylphenol and 3.1 g (0.025 mole) of 2,6-dimethylphenol is dissolved in 100 ml of methylene chloride, and 0.01 g of ferric chloride is added The solution is heated at 40° C. for 2 hours, and the solvent is removed followed by washing of the solid residue with 100 ml of carbon tetrachloride to yield 3.8 g of solid which melts at 130° C.–150° C. Analysis of the solid by HNMR and liquid chromatography indicates it to contain approximately 90 percent of a 2,4-dibenzylphenol product represented by the formula:

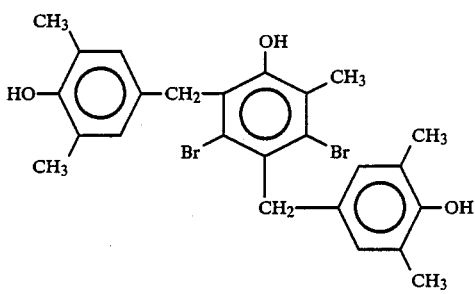

2 percent of a 4-benzylphenol product represented by the formula:

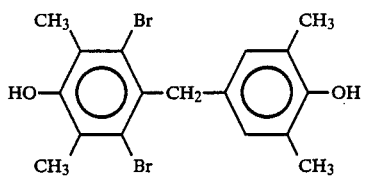

and 7 percent of a 2,4,6-tribenzylphenol product represented by the formula:

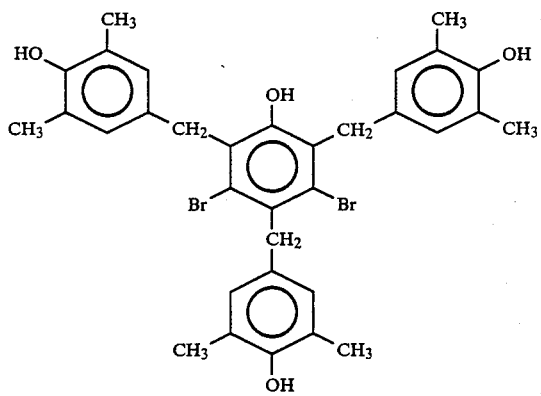

EXAMPLE 2

A. Bromination of Tribromomesitol

Following the procedure of Example 1 in a 3-liter flask and substituting 373 g (1.0 mole) tribromomesitol for mesitol, 154 ml (3.0 moles) of bromine and 1.0 liter of 1,1,2-trichloroethane are added to the flask and the contents are stirred and heated for 3 hours. Analysis of the 262.8 g of white solid product by proton NMR and liquid chromatography indicates the product to contain 85 percent (area percent) of 2,4-bis-(bromomethyl)-3,5-dibromo-6-methylphenol; 5 percent of 4-bromomethyl-3,5-dibromo-2,6-dimethyl phenol and 5 percent 2,4,6-tris(bromomethyl)-3,5-dibromophenol.

B. Alkylation of 2,4-Bis(bromomethyl)-3,5-dibromo-6-methylphenol

A 250-g portion of solid product from Part A and 169 g (1.38 moles) of 2,6-dimethylphenol is dissolved in 2.0 liters of methylene chloride, and 0.3 g of ferric chloride is added The solution is heated at 40° C. for 2 hours. At the end of this period, 1.5 liters of the solvent is removed by distillation under nitrogen. The residual solution is cooled and filtered to recover 165 g of solid product similar to that obtained in Part B of Example 1.

EXAMPLE 3

A. Bromination of 3,4,5-Tribromo-2.6-dimethylphenol

A 35.9-g portion (0.1 mole) of 3,4,5-tribromo-2,6-dimethylphenol is slurried in 100 ml of 1,1,2-trichloroethane, and 20.5 ml (0.4 mole) of bromine is then added to the slurry at 20° C. The slurry is then heated with stirring to 90° C.–94° C. C for 3.5 hours. The desired product is recovered as described in Example 1 and analysis of the product indicates it to comprise the following 85 percent of 2-bromomethyl-3,4,5-tribromo-6-methylphenol and 7 percent 2,6-bis(bromomethyl)-3,4,5-tribromophenol.

B. Alkylation of 2-bromomethyl-3,4,5-tribromo-6-methylphenol

A 4.4-g portion of the solid from part A of this Example is dissolved in 100 ml of methylene chloride after which are successively added 1.8 g of 2,6-dimethylphenol (0.015 mole) and 0.01 g of ferric chloride. The resulting solution is refluxed at 40° C. for 2 hours, and the solvent is removed to provide a brown solid which is washed with 100 ml of water to yield 4.3 g of solid which melts at 171° C.–177° C. Analysis of the solid by HNMR and liquid chromatography indicates that the solid contains more than 80 percent of the brominated 2-benzylphenol product represented by the formula:

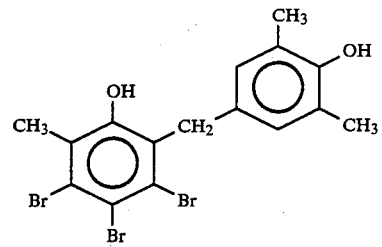

4 percent of 3,4,5-tribromo-2,6-dimethylphenol and 14 percent of the 2,6-dibenylphenol product represented by the formula:

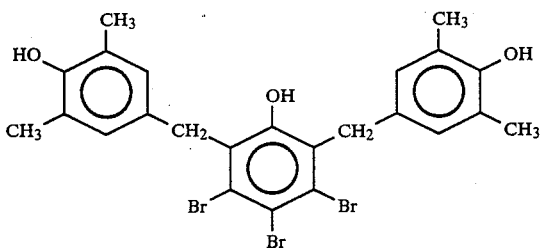

EXAMPLE 4

A. Bromination of Tetrabromotetramethylbiphenol

A 55.8-g (0.1 mole) portion of tetrabromotetramethylbiphenol is slurried in 100 ml of 1,1,2-trichloroethane and 20.5 ml of bromine (0.4 mole) is added with stirring at 20° C. The mixture is heated to 90° C.–95° C. for 3.5 hours. Thereafter unreacted bromine is removed until the reaction solution is reduced in volume to 50 ml. The reaction solution is then cooled and filtered to yield 62.9 g of an off-white solid which melts at 215° C.–222° C. and contains 63 percent (area percent) of 3,3',5-tris(-bromomethyl)-2,2'6,6'-tetrabromo-5'-methyl-[1,1'-biphenyl]-4,4'-diol; 33 percent of 3,3'-bis(bromomethyl)-2,2'6,6'-tetrabromo-5,5'-dimethyl-[1,1'-biphenyl]-4,4'-diol; and 3 percent of 3-bromomethyl-2,2', 6,6'-tetrabromo-3',5,5'-trimethyl-[1,1'-biphenyl]-4,4'-diol.

B. Alkylation of the Product of Part A

A 7.2-g portion of the brominated product of part A is dissolved in 100 ml of methylene chloride, and 3.7 g (0.03 mole) of 2,6-dimethylphenol and 0.03 g of ferric chloride are successively added to the reaction mixture. The resulting solution is refluxed for 2 hours, and solvent is removed to provide a solid which is washed with 100 ml of water to yield 7.6 g of a brown solid which melts at 87° C.–94° C. Analysis of the brown solid by HNMR indicates it to be primarily an alkylated MBDB phenols corresponding to the structural formula:

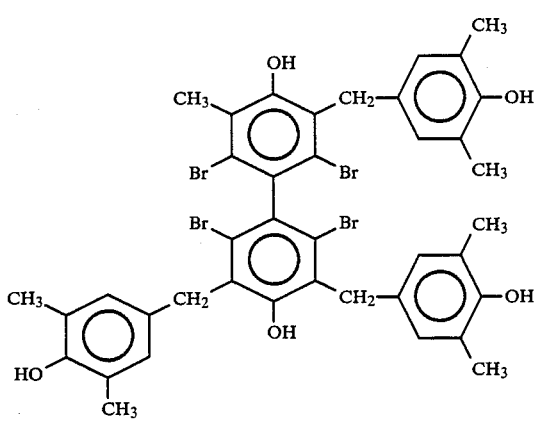

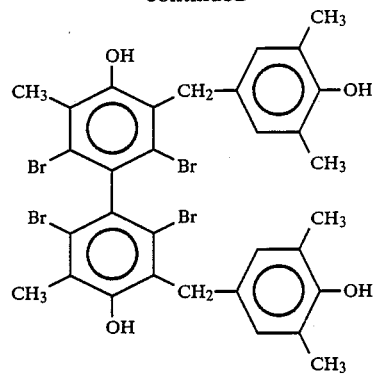

EXAMPLE 5

A 0.50-g portion (1.3 mmoles) of ortho-tribromomesitol (prepared by the procedure of Fires et al., Ann., 353, 335–356 (1907)) is dissolved in 50 ml of methylene chloride, and 0.17 g of 2,6-dimethylphenol is added, followed by 0.01 g of ferric chloride. The solution is heated at 40° C. for 1.0 hour. Removal of the solvent affords 0.57 g of brown solid which melts at 178° C.–181° C., and has spectral properties corresponding to the following structural formula:

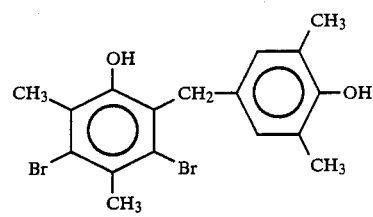

What is claimed is:

1. A thermally stable methylene-bridged polyphenol having (1) at least two phenolic hydroxyl moieties which are substituted on different aromatic rings wherein at least one phenolic hydroxyl is in a ring position ortho to a methylene bridge, and (2) at least two halogens, each of which is substituted on an aromatic ring in a position meta to a phenolic hydroxyl.

2. The polyphenol of claim 1 wherein the polyphenol has at least three phenolic hydroxyl moieties which are substituted on different aromatic rings.

3. The polyphenol of claim 1 wherein halo is bromo.

4. The polyphenol of claim 1 wherein the polyphenol has at least two phenolic moieties represented by the structural formula:

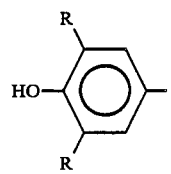

wherein each R is independently hydrogen, alkyl having from 1 to 12 carbons, cycloalkyl having from 5 to 10 carbons, aralkyl having from 8 to 12 carbons and alkoxy having 1 to 6 carbons.

5. The polyphenol of claim 1 wherein the polyphenol has a divalent connecting halogenated phenolic moiety as represented by the structural formula:

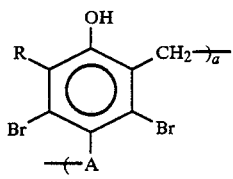

wherein A is —CH$_2$— or a covalent bond, R is as previously defined and "a" is a whole number from 1 to 10.

6. The polyphenol of claim 1 wherein the polyphenol is represented by the structural formula:

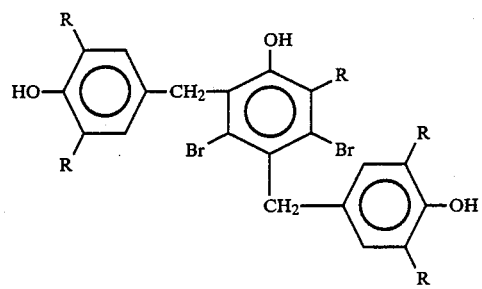

wherein R is methyl or ethyl.

7. The polyphenol of claim 1 wherein the polyphenol is represented by the structural formula:

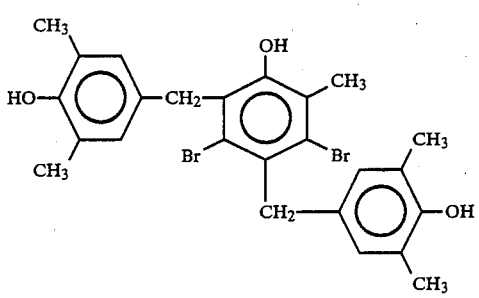

8. The polyphenol of claim 1 wherein the polyphenol is represented by the structural formula:

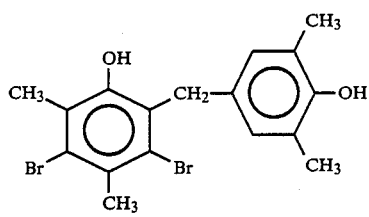

9. The polyphenol of claim 1 wherein the polyphenol is represented by the structural formula:

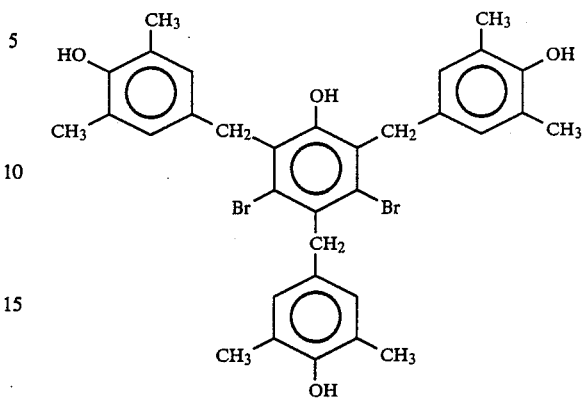

10. The polyphenol of claim 1 wherein the polyphenol is represented by the structural formula:

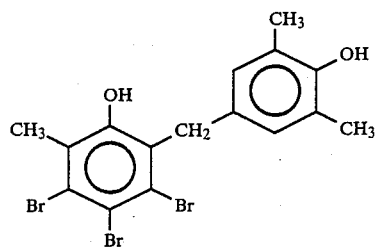

11. The polyphenol of claim 1 wherein the polyphenol is represented by the structural formula:

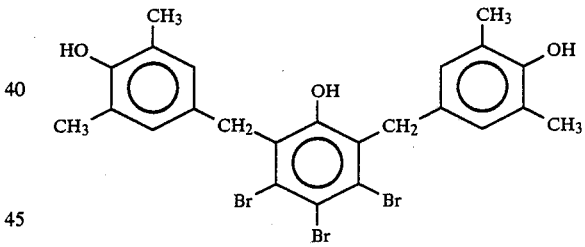

12. A process for preparing the polyphenol of claim 1 which process comprises contacting (1) a substituted phenol having at least one halogen substituted on the aromatic ring in a position meta to the phenolic hydroxyl and at least one halomethyl group substituted on the aromatic ring in a position ortho or para to the phenolic hydroxyl with (2) an o,o-dialkylphenol having hydrogen on the aromatic ring position which is para to the phenolic hydroxyl in the presence of an alkylation catalyst under conditions sufficient to form the polyphenol.

* * * * *